United States Patent
Wang et al.

(10) Patent No.: US 11,423,535 B2
(45) Date of Patent: Aug. 23, 2022

(54) METHOD AND DEVICE FOR STATE DISPLAY DURING VENTILATION PROCESS

(71) Applicant: SHENZHEN MINDRAY BIO-MEDICAL ELECTRONICS CO., LTD., Shenzhen (CN)

(72) Inventors: Huihua Wang, Shenzhen (CN); Yu Chen, Shenzhen (CN); Ruiling Pan, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 210 days.

(21) Appl. No.: 16/818,851

(22) Filed: Mar. 13, 2020

(65) Prior Publication Data
US 2020/0219257 A1     Jul. 9, 2020

Related U.S. Application Data

(63) Continuation of application No. PCT/CN2017/101730, filed on Sep. 14, 2017.

(51) Int. Cl.
| | |
|---|---|
| *G06T 7/00* | (2017.01) |
| *A61B 5/08* | (2006.01) |
| *A61B 5/091* | (2006.01) |
| *A61B 5/00* | (2006.01) |
| *G06T 7/13* | (2017.01) |

(52) U.S. Cl.
CPC .............. *G06T 7/0012* (2013.01); *A61B 5/08* (2013.01); *A61B 5/0816* (2013.01); *A61B 5/091* (2013.01); *A61B 5/742* (2013.01); *G06T 7/13* (2017.01); *G06T 2207/30061* (2013.01)

(58) Field of Classification Search
CPC ................ G06T 7/0012; G06T 7/13; G06T 2207/30061; A61B 5/0816; A61B 5/091; A61B 5/742; A61B 5/08; A61M 16/00; G16H 20/40; G16H 40/63; G16H 50/20
See application file for complete search history.

(56) References Cited

U.S. PATENT DOCUMENTS

| | | |
|---|---|---|
| 6,099,481 A | 8/2000 | Daniels et al. |
| 2007/0199566 A1 | 8/2007 | Be eri |
| (Continued) | | |

FOREIGN PATENT DOCUMENTS

| | | |
|---|---|---|
| CN | 101360537 A | 2/2009 |
| CN | 101636110 A | 1/2010 |
| (Continued) | | |

OTHER PUBLICATIONS

English Translation of JP3468574B2 (Year: 2003).*
(Continued)

*Primary Examiner* — Jon Chang
(74) *Attorney, Agent, or Firm* — Bayes PLLC

(57) ABSTRACT

The present disclosure relates to medical instruments, and in particular to a method and device for state display during a ventilation process, a ventilator, a computer device, and a computer-readable storage medium. A method for state display during a ventilation process can include determining, by a processor, a monitoring parameter regarding a user. The method can also include displaying a first image corresponding to the monitoring parameter according to a pre-set correlation.

20 Claims, 6 Drawing Sheets

---

1101 — Determining a monitoring parameter regarding a user, and determine a respiratory state of the user 1102 — Displaying a first image corresponding to the monitoring parameter according to a pre-set correlation, and displaying a continuous change in a third transparency of a third lung image according to a gas moving direction in the respiratory state

(56) References Cited

U.S. PATENT DOCUMENTS

| | | | | |
|---|---|---|---|---|
| 2009/0024008 A1* | 1/2009 | Brunner | ............... | A61B 5/743 600/301 |
| 2013/0150734 A1* | 6/2013 | Orr | ............... | A61M 16/0666 600/484 |
| 2013/0156267 A1* | 6/2013 | Muraoka | ............... | G06T 7/0016 382/103 |
| 2016/0243324 A1 | 8/2016 | Doyle et al. | | |

FOREIGN PATENT DOCUMENTS

| | | | | |
|---|---|---|---|---|
| CN | 103080942 A | 5/2013 | | |
| CN | 106344021 A | 1/2017 | | |
| JP | 3468574 B2 * | 11/2003 | ............ | A61B 5/087 |

OTHER PUBLICATIONS

Extended European Search Report issued in related European Application No. 17924809.1, dated Mar. 15, 2021, 8 pages.
International Search Report issued in corresponding International Application No. PCT/CN2017/101730, dated May 31, 2018, 7 pages.
First Office Action issued in related Chinese Application No. 201780094802.5, dated Feb. 17, 2022, 9 pages.

* cited by examiner

METHOD AND DEVICE FOR STATE DISPLAY DURING VENTILATION PROCESS

CROSS-REFERENCE TO RELATED APPLICATION

This application is a bypass continuation of PCT application number PCT/CN2017/101730, filed on Sep. 14, 2017, the entirety of which is hereby incorporated herein by reference.

TECHNICAL FIELD

The present disclosure relates to the technical field of medical instruments, and in particular to a method and device for state display during a ventilation process, a ventilator, a computer device, and a computer-readable storage medium.

BACKGROUND

In modern clinical medicine, ventilators have become an essential medical device for implementing spontaneous ventilation. At present, ventilators have been widely applied to various medical scenarios, such as respiratory failure from various reasons, respiration management in anesthesia during major surgery, respiratory support therapy, and emergency resuscitation, and ventilators play a very important role in the field of modern medical field.

However, with the popularization of ventilators, some disadvantages of ventilators are also exposed due to various on-site application requirements:

1. The trend of changes in lung state during ventilation of a patient cannot be intuitively observed, which is not beneficial for the treatment of the patient and also affects the use experience of a ventilator; and 2. Timely adjustment of the ventilation volume cannot be provided as desired, and often requires a physician or a nurse to make adjustment according to changes in patient's conditions, which results in low timeliness and also brings the risk of estimated misdiagnoses.

SUMMARY

Embodiments of the present disclosure provide a method and device for state display during a ventilation process, a ventilator, a computer device, and a computer-readable storage medium, configured for carrying out intuitive image display on a ventilation state during a ventilation process and improve the accurate determination of the ventilation state, thereby facilitating timely adjustment of a respiratory therapy strategy.

In view of this, a first aspect of the present disclosure provides a method for state display during a ventilation process, comprising:

determining a monitoring parameter regarding a user; and displaying a first image corresponding to the monitoring parameter according to a pre-set correlation.

A second aspect of the present disclosure provides a device for state display during a ventilation process, comprising:

a first processor configured to determine a monitoring parameter regarding a user; and a first display configured to display a first image corresponding to the monitoring parameter according to a pre-set correlation.

A third aspect of the present disclosure provides a ventilator, which may comprise the foregoing device for state display during a ventilation process provided in the second aspect of the present disclosure.

A fourth aspect of the present disclosure provides a computer device comprising a processor which is configured for executing a computer program stored in a memory to implement the following:

determining a monitoring parameter regarding a user; and displaying a first image corresponding to the monitoring parameter according to a pre-set correlation.

A fifth aspect of the present disclosure provides a computer-readable storage medium with a computer program stored therein, the computer program is executed by a processor to implement the following:

determining a monitoring parameter regarding a user; and displaying a first image corresponding to the monitoring parameter according to a pre-set correlation.

As can be seen from the foregoing technical solutions, certain embodiments of the present disclosure have the following advantages:

Certain embodiments of the present application provide a method for state display during a ventilation process. During a ventilation process of a user, by means of determining a monitoring parameter regarding the user and displaying a first image corresponding to the monitoring parameter according to a pre-set correlation, the intuitive image display of a ventilation state during a ventilation process of the user can be provided to a physician or a nurse monitoring a ventilator so as to improve the accurate determination of the ventilation state of the user by the physician or nurse, thereby facilitating timely adjustment of a respiratory therapy strategy and also facilitating improvement of ventilator-based therapy experience of the user.

BRIEF DESCRIPTION OF THE DRAWINGS

In order to illustrate the technical solutions in certain embodiments of the present disclosure more clearly, a brief introduction to the drawings required for certain embodiments will be provided below. Obviously, the drawings in the following description are merely some of the embodiments of the present disclosure, and those of ordinary skill in the art would also obtain other drawings according to these drawings without involving any inventive effort.

DETAILED DESCRIPTION OF EMBODIMENTS

Figure 1:
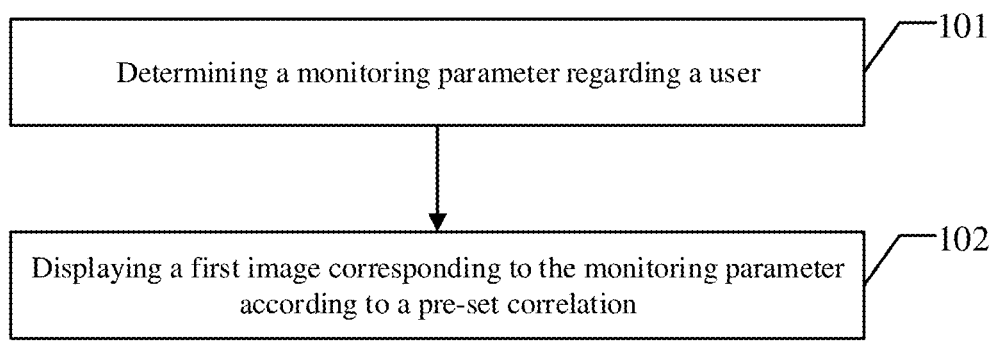
FIG. 1 is a schematic diagram of an embodiment of a method for state display during a ventilation process according to an embodiment of the present disclosure.

Embodiments of the present disclosure provide a method and device for state display during a ventilation process, a ventilator, a computer device, and a computer-readable storage medium, configured for carrying out intuitive image display on a ventilation state during a ventilation process and improve the accurate determination of the ventilation state, thereby facilitating timely adjustment of a respiratory therapy strategy.

To make the solutions of the present disclosure more comprehensible to a person skilled in the art, the technical solutions of certain embodiments of the present application will be described below clearly and comprehensively in conjunction with the drawings of certain embodiments of the present disclosure. Clearly, the embodiments described are merely some embodiments of the present disclosure and are not all the possible embodiments. Based on the embodiments described herein, all other embodiments that would be obtained by those of ordinary skill in the art without expending inventive effort shall all fall within the scope of protection of the present disclosure.

The terms "first", "second", "third", "fourth", etc. (if any) in the specification and the claims and the above-mentioned drawings are used to distinguish similar objects and are not necessarily used to describe a specific order or sequence. It should be understood that the terms used as such is interchangeable where appropriate, so that the embodiments described herein can be implemented in an order other than what is illustrated or described herein. Moreover, the terms "comprise" and "have" or any variation of such terms are intended to cover a non-exclusive inclusion. For example, a process, method, product or device that includes a series of steps or units not only includes those steps or units specified expressly, but also includes other steps or units that are not specified expressly or are inherent to the process, method, product or device.

Generally, a ventilator is often used to provide respiratory support to an inpatient and is characterized by a variety of ventilation modes, highly flexible parameter settings, and complete ventilation monitoring display. The ventilator is also provided with various diagnostic tools and can be used to provide a patient with the most effective ventilation therapy.

However, during a process of using a ventilator to provide respiratory support to a user, a physician or a nurse usually provides ventilation therapy to an inpatient according to experience, and the ventilator cannot provide a change trend of ventilation volume of the inpatient, providing no benefit to corresponding adjustment of the ventilation volume and affecting therapeutic experience of the inpatient.

Therefore, the present disclosure provides a method for state display during a ventilation process. During a process of treating a user with a ventilator, a monitoring parameter regarding the user is determined, and a first image corresponding to the monitoring parameter may be displayed, so that the monitoring parameter during a ventilation process can be intuitively, visually, and vividly presented to a physician or nurse monitoring the ventilator. The physician or nurse can accurately determine a ventilation state of the user according to the intuitive presentation of the monitoring parameter on the first image, thereby facilitating timely adjustment of a respiratory therapy strategy of the user and providing significant benefit to the evaluation of the effect of ventilation therapy provided to the user, determination of the user's conditions, and the like.

For ease of understanding, specific procedures of certain embodiments of the present disclosure are described below. Referring to FIG. 1, in certain embodiments of the present disclosure, an embodiment of a method for state display during a ventilation process comprises the following:

101. A monitoring parameter regarding a user is determined.

In this embodiment, the user is a monitored person, for example, a patient. When the user's respiratory organs cannot complete normal gas exchange, a ventilator may be used to provide ventilation therapy to provide respiratory support to the user. During a ventilation process of the user, a corresponding detector is used to determine the monitoring parameter regarding the user.

102. A first image corresponding to the monitoring parameter is displayed according to a pre-set correlation.

In this embodiment, after the monitoring parameter regarding the user is determined, the first image corresponding to the monitoring parameter may be displayed according to the pre-set correlation.

Specifically, during a ventilation process of the user, one or more monitoring parameters regarding a ventilation state of the user may be monitored. The one or more monitoring parameters may separately correspond to one pre-set correlation. Each pre-set correlation may be a correlation between a corresponding monitoring parameter and a corresponding first image. When a same monitoring parameter is in different cases, for example, the monitoring parameter is normal or abnormal, there are distinct features on the displayed first image. Therefore, a corresponding state corresponding to the monitoring parameter may be acquired according to the displayed first image.

In this embodiment, during a ventilation process of a user, a monitoring parameter regarding the user is determined, and a first image corresponding to the monitoring parameter may be displayed, so as to provide a physician or nurse monitoring a ventilator with intuitive image display of a ventilation state during the ventilation process of the user and improve the accurate determination of the ventilation state of the user by the physician or nurse, thereby facilitating timely adjustment of a respiratory therapy strategy and helping improve ventilator-based treatment experience for the user.

It may be understood that in the present disclosure, the monitoring parameter may comprise at least one of ventilation volume, lung compliance, thoracic compliance, or target work of breathing. Different first images may be displayed to indicate changes caused by at least one of the ventilation volume, the lung compliance, the thoracic compliance, and the target work of breathing. Therefore, to distinguish between different displayed first images caused by the ventilation volume, the lung compliance, the thoracic compliance, and the target work of breathing, corresponding pre-set correlations may be separately set. A first pre-set correlation may be set for the ventilation volume, a second pre-set correlation may be set for the lung compliance, a third pre-set correlation may be set for the thoracic compliance, a third pre-set correlation may be set for the target work of breathing, and a fourth pre-set correlation may be set for the target work of breathing. The pre-set correlations are separately described below.

Figure 2:
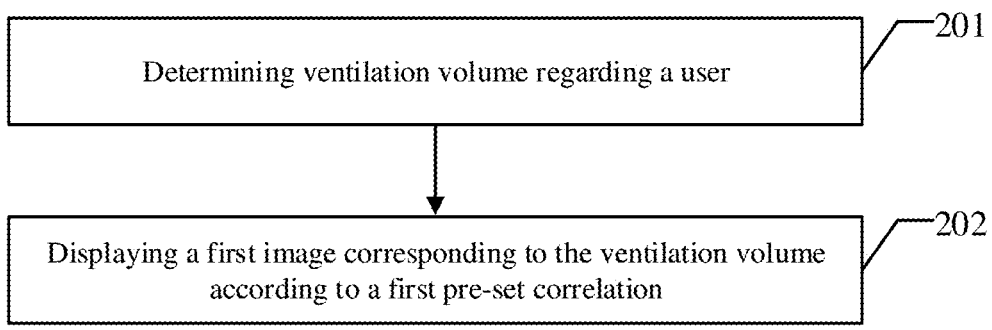
FIG. 2 is a schematic diagram of another embodiment of a method for state display during a ventilation process according to an embodiment of the present disclosure.

Referring to FIG. 2, in certain embodiments of the present disclosure, another embodiment of a method for state display during a ventilation process comprises the following.

201. The ventilation volume regarding a user is determined.

In this embodiment, during a ventilation process of the user, corresponding monitoring parameter obtained by a corresponding detector may be used to determine the ventilation volume of the user, which is the ventilation regarding the user.

Specifically, to indicate the ventilation volume of the user in real time, the ventilation volume may be ventilation volume of the user within one respiratory cycle. Optionally, the ventilation volume may be ventilation volume of the user during one exhalation process. For example, the ventilation volume of the user may be determined according to end-tidal carbon dioxide ($PETCO_2$). The end-tidal carbon dioxide has high sensitivity and is determined by a carbon dioxide output and ventilation volume of the body. When the end-tidal carbon dioxide is excessively high, it may indicate that the ventilation volume of the user is inadequate. When the end-tidal carbon dioxide is excessively low, it may indicate that the ventilation volume of the user is excessive.

It may be understood that in this embodiment, in addition to the use of the end-tidal carbon dioxide to determine the ventilation volume of the user, during actual application, another manner may be used provided that it can be determined according to the determined ventilation volume whether a ventilation requirement of the user is satisfied.

It should be noted that in addition to the ventilation volume within one respiratory cycle described above, the ventilation volume in this embodiment may be other ventilation volume, for example, average ventilation volume within a pre-set quantity of previous respiratory cycles, and may be specifically set as required. This is not limited herein.

202. A first image corresponding to the ventilation volume is displayed according to a first pre-set correlation.

In this embodiment, after the ventilation volume of the user is determined, the first image corresponding to the ventilation volume may be displayed according to the first pre-set correlation.

For example, the first image may comprise a first lung image. The first lung image for intuitive presentation may be prestored in a device for state display during a ventilation process to which a method of the present disclosure is applicable. The first lung image may be drawn according to the form of a human lung, and for example, may visually comprise two lung lobes, a trachea, and a left bronchus and a right bronchus that are separately located in the two lung lobes. It should be noted that in this embodiment, the first lung image may be obtained through real-time modeling. This is not specifically limited herein.

Moreover, the first pre-set correlation regarding the ventilation volume may be prestored according to the value of the ventilation volume. During a process of providing ventilation therapy the user, both inadequate ventilation volume and excessive ventilation volume have adverse effects. The inadequate ventilation volume may lead to carbon dioxide retention to cause hypercapnia or the like. The excessive ventilation volume may cause hypocapnia. In this way, a pre-set ventilation threshold matching the user may be set according to the user's personal conditions. Once the ventilation volume of the user exceeds the pre-set ventilation threshold, it indicates that the ventilation volume is excessive, or otherwise, it indicates that the ventilation volume is inadequate. Two first lung images may be separately set based on the inadequate ventilation volume and the excessive ventilation volume. The first pre-set correlation is a correlation between the inadequate ventilation volume or the excessive ventilation volume and a differentiation between the two first lung images, so that a monitor of a ventilator can determine the value of the ventilation volume of the user according to a displayed first lung image and make a timely adjustment.

It may be understood that in this embodiment, according to the user's personal conditions, the pre-set ventilation threshold may be a value range in addition to a value to provide the ventilation volume with a large room for adjustment.

It should be noted that in this embodiment, a first lung image may further be set when the ventilation volume of the user is normal. The first lung image has a differentiation from a corresponding first lung image when the ventilation volume is abnormal to facilitate corresponding determination according to the differentiation. This is not specifically limited herein.

During actual application, the first pre-set correlation may be a correlation between the value of ventilation volume and the position of a pre-set plot on a first lung image, so that the position of a pre-set plot on a displayed first lung image may be used to indicate the value of ventilation volume. The pre-set plot may be, for example, the shape of a lung contour on the first lung image. However, the size, the shape, the format, and the position displayed on the first lung image may be changed according to the value of the ventilation volume, and may specifically need to be correspondingly designed, provided that the displayed first lung image can be used to intuitively learn about the value of the ventilation volume.

Figure 3:
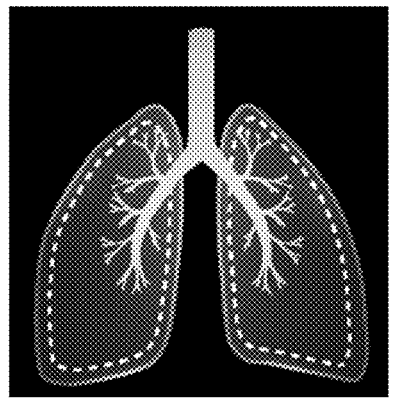
FIG. 3 is a schematic diagram of image display when the ventilation volume is high according to an embodiment of the present disclosure.
Figure 4:
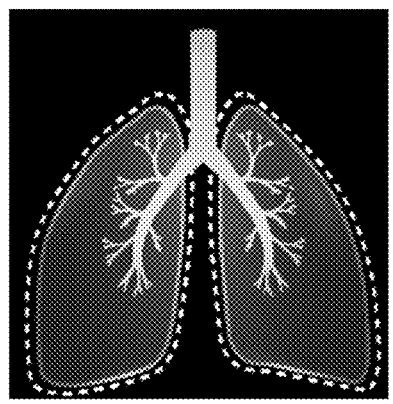
FIG. 4 is a schematic diagram of image display when the ventilation volume is low according to an embodiment of the present disclosure.

For example, it is assumed that the pre-set plot is a dotted line consistent with the lung contour. When the ventilation volume is excessive (or the end-tidal carbon dioxide is excessively low), as shown in FIG. 3, a dotted-line first lung image set at an inner edge of the lung contour may be displayed. When the ventilation volume is inadequate (or the end-tidal carbon dioxide is excessively high), as shown in FIG. 4, a dotted-line first lung image set at an outer edge of the lung contour may be displayed, so that different displayed positions of the dotted lines on the first lung image are used to distinguish between values of the ventilation volume. It should be noted that the format of the pre-set plot and the positions displayed based on the values of the ventilation volume in this embodiment are only examples for description. During actual application, other methods may be used to determine according to the displayed first lung image whether ventilation volume is inadequate or excessive. This is not specifically limited herein.

Further, in this embodiment, to prevent a problem such as undesirable ventilation therapy caused by inadequate ventilation volume or excessive ventilation volume, in addition to intuitive display of whether ventilation volume is adequate, a ventilation adjustment prompt corresponding to the ventilation volume may be output, to enable a monitor such as a physician or nurse of the ventilator to timely adjust the ventilation volume of the user as required, thereby preventing carbon dioxide retention or excessive ventilation. When the ventilation volume is inadequate, a prompt of increasing the ventilation volume may be output. That is, gas supply to the user is increased. When the ventilation volume is excessive, a prompt of reducing the ventilation volume may be output. That is, gas supply to the user is reduced. A manner of the prompt may comprise, but is not limited to, at least one of a voice prompt, a multimedia prompt, or a light prompt.

It may be understood that during a process of providing ventilation therapy the user, another position in the user's lung or thoracic cavity may have other different states. These states coordinate with the ventilation volume of the user to jointly affect a respiration process of the user. Therefore, the display of monitoring parameters corresponding to these states is provided to further facilitate the adjustment of a respiratory therapy strategy of the user and the evaluation of the effect of respiratory therapy. These related states are described below in detail.

Figure 5:
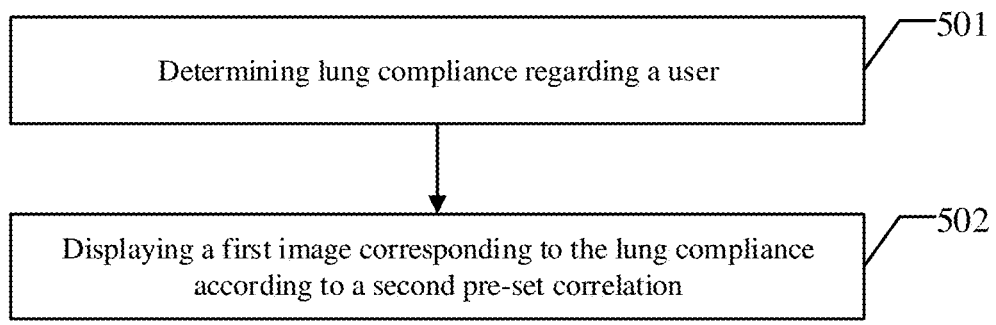
FIG. 5 is a schematic diagram of another embodiment of a method for state display during a ventilation process according to an embodiment of the present disclosure.

Referring to FIG. 5, in certain embodiments of the present disclosure, another embodiment of a method for state display during a ventilation process comprises the following.

501. The lung compliance regarding a user is determined.

In this embodiment, during a ventilation process of the user, corresponding monitoring parameter obtained by different detectors may be used to determine the lung compliance regarding the user, that is, the lung compliance of the user.

Specifically, the lung compliance is a change in a lung volume caused by a change in a unit pressure and can indicate the elasticity of the user's lung tissue. To indicate the lung compliance of the user in real time, the lung compliance may be the lung compliance of the user within one respiratory cycle, and optionally, may be static lung compliance.

It should be noted that in addition to the lung compliance within one respiratory cycle described above, the lung compliance in this embodiment may be, for example, average lung compliance within a pre-set quantity of previous respiratory cycles, and may be specifically set as required. This is not limited herein.

502. A first image corresponding to the lung compliance is displayed according to a second pre-set correlation.

In this embodiment, after the lung compliance of the user is determined, the first image corresponding to the lung compliance may be displayed according to the second pre-set correlation.

Specifically, the second pre-set correlation regarding the lung compliance may be prestored according to the value of the lung compliance. The value of the lung compliance may be used to diagnose whether the user's lung tissue has possible abnormalities. The static lung compliance is used as an example for description. When the static lung compliance is low, the user may have a restrictive lung disease, an alveolar filling disorder or the like. If the user has emphysema, damage to alveolar walls causes less elastic tissue (that is, reduced elastic resistance) in lung tissue, and the static lung compliance increases. In this way, a pre-set lung compliance threshold may be set according to the value of normal lung compliance. Once the lung compliance of the user exceeds the pre-set lung compliance threshold, it indicates that the lung compliance of the user is high. Otherwise, it indicates that the lung compliance of the user is low.

For example, the first image may comprise a second lung image. Two second lung images may be separately set based on high lung compliance and low lung compliance. The second pre-set correlation is a correlation between the high or low lung compliance and a differentiation between the two second lung images, so that a monitor of a ventilator can determine the value of the lung compliance of the user according to a displayed second lung image and make appropriate determination. The size of the second lung image is remained unchanged.

It may be understood that in this embodiment, the pre-set lung compliance threshold may be a value range in addition to a value to provide the determination of the value of the lung compliance with a large room.

It should be noted that in this embodiment, a second lung image may further be set when the lung compliance of the user is normal. The second lung image has a differentiation from a corresponding second lung image when the lung compliance is abnormal to facilitate corresponding determination according to the differentiation. This is not specifically limited herein.

Further, in this embodiment, the displaying a first image corresponding to the lung compliance according to a second pre-set correlation may comprise:

Displaying the second lung image corresponding to the lung compliance according to a correlation between the value of the lung compliance and the color of a lung contour in the second lung image; and/or Displaying the second lung image corresponding to the lung compliance according to a correlation between the value of the lung compliance and the thickness of a lung contour in the second lung image; and/or Displaying the second lung image corresponding to the lung compliance according to a correlation between the value of the lung compliance and a first transparency of a second lung image.

Figure 6:
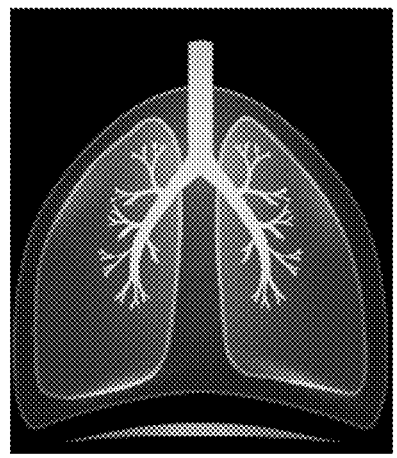
FIG. 6 is a schematic diagram of image display when the ventilation is normal according to an embodiment of the present disclosure.
Figure 7:
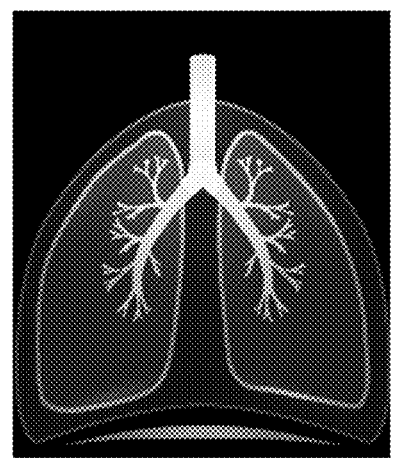
FIG. 7 is a schematic diagram of image display when the lung compliance is high and the thoracic compliance is high according to an embodiment of the present disclosure.
Figure 8:
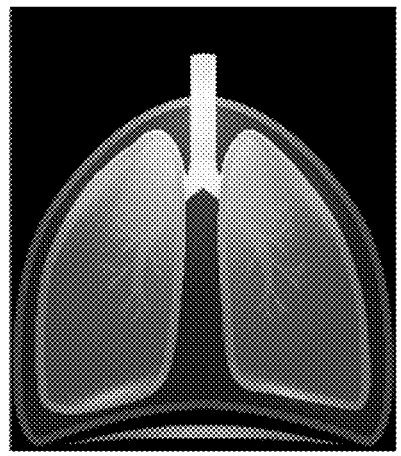
FIG. 8 is a schematic diagram of image display when the lung compliance is low and the thoracic compliance is low according to an embodiment of the present disclosure.

Specifically, the color of the lung contour on the displayed second lung image may be used to indicate the value of the lung compliance. For example, when the lung compliance is high, the color of the lung contour on the displayed second lung image may be orange. When the lung compliance is low, the color of the lung contour on the displayed second lung image may be green; and/or the thickness of the lung contour on the displayed second lung image may be used to indicate the value of the lung compliance. For example, when the lung compliance is high, the line of the lung contour on the displayed second lung image may become slightly thinner than that on the original normal lung image. When the lung compliance is low, the line of the lung contour on the displayed second lung image may become slightly thicker than that on the original normal lung image; and/or the transparency of the displayed second lung image may be used to indicate the value of the lung compliance. For example, when the lung compliance is low, compared with FIG. 6 (the normal lung image), as shown in FIG. 7, the transparency of the displayed second lung image may be less than the transparency of the original normal lung image, that is, an adjustment is made to obtain a first transparency, so that the left and right bronchi and the like on the displayed second lung image look clearer, and different parts on the second lung image have more distinct contrast. For example, when the lung compliance is high, compared with FIG. 6, as shown in FIG. 8, the transparency of the displayed second lung image may be greater than the transparency of the original normal lung image, that is, an adjustment is made to obtain another first transparency, so that the left and right bronchi and the like on the displayed second lung image look more blurred as if the second lung image is covered by a layer of fog. Different parts on the second lung image have less distinct contrast. It should be noted that the foregoing content in this embodiment is only an example for description. During actual application, what colors are to be used and how to adjust the thickness or transparency on the second lung image for corresponding indication may be designed according to an actual requirement. This is not specifically limited herein.

It may be understood that in addition to the content described above, during actual application, for the second pre-set correlation in this embodiment, other manners may be separately used or used in combination. For example, regardless of the value of the lung compliance, when the lung compliance is abnormal, the lung contour on the displayed second lung image may turn orange, and the thickness of the line on the displayed lung contour and the transparency are correspondingly combined to indicate the value of the lung compliance, provided that the displayed second lung image can clearly indicate high or low lung compliance. In this case, the thickness of the line of the lung contour on the displayed second lung image may be not obtained by making a change to the original normal lung image. Instead, while there are differentiations in color, as shown in FIG. 7 and FIG. 8 (the color of the lung contour in the figures is not shown), the line of the lung contour when the lung compliance is low may be thicker than the line of the lung contour when the lung compliance is high. This is not specifically limited herein.

It should be noted that in this embodiment, both the ventilation volume and the lung compliance of the user may be displayed on a corresponding first image. The states of the ventilation and the lung compliance of the user may be presented on the same lung image. That is, the ventilation volume and the lung compliance are correspondingly indicated on the same lung image, that is, features of both the first lung image and the second lung image are provided. Alternatively, the states may be not presented on the same lung image. That is, the first lung image and the second lung image are separately displayed. This is not specifically limited herein.

Further, based on the foregoing embodiments, the thoracic compliance of the user during a ventilation process may be correspondingly indicated to provide more information, and a device for state display during a ventilation process has more functions. Details are described below.

Figure 9:
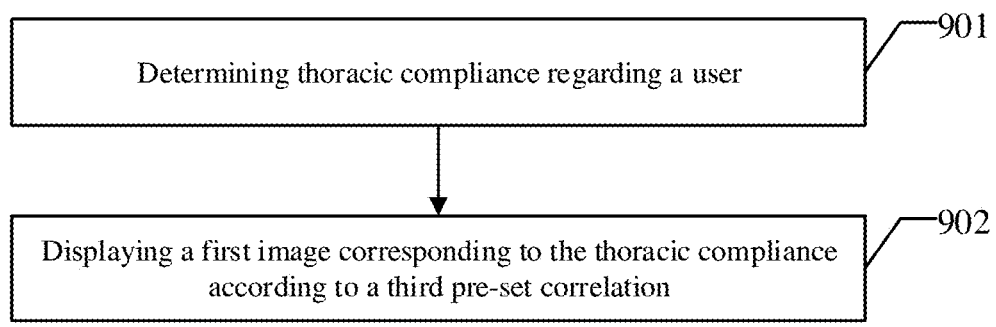
FIG. 9 is a schematic diagram of another embodiment of a method for state display during a ventilation process according to an embodiment of the present disclosure.

Referring to FIG. 9, in certain embodiments of the present disclosure, another embodiment of a method for state display during a ventilation process comprises the following.

901. The thoracic compliance regarding a user is determined.

In this embodiment, during a ventilation process of the user, corresponding monitoring parameter obtained by a corresponding detector may be used to determine the thoracic compliance regarding the user, that is, the thoracic compliance of the user.

To indicate the thoracic compliance of the user in real time, the thoracic compliance may be the thoracic compliance of the user within one respiratory cycle.

It should be noted that in addition to the thoracic compliance within one respiratory cycle described above, the thoracic compliance in this embodiment may be, for example, average thoracic compliance within a pre-set quantity of previous respiratory cycles, and may be specifically set as required. This is not limited herein.

In this embodiment, for a manner of determining the thoracic compliance of the user, reference may be made to the prior art. Details are not described again herein.

902. A first image corresponding to the thoracic compliance is displayed according to a third pre-set correlation.

In this embodiment, after the thoracic compliance of the user is determined, the first image corresponding to the thoracic compliance may be displayed according to the third pre-set correlation.

For example, the first image may comprise a first thoracic image. The first thoracic image for intuitive presentation may be prestored in a device for state display during a ventilation process to which a method of the present disclosure is applicable. As shown in FIG. 6, the first thoracic image may be drawn according to a human's chest wall form, and a lung image may be drawn on the first thoracic image according to relative positions of the human's lung and chest wall, to enable visual and vivid presentation. It should be noted that in this embodiment, the first thoracic image may be obtained through real-time modeling. This is not specifically limited herein.

Moreover, the third pre-set correlation regarding the thoracic compliance may be prestored according to the value of the thoracic compliance. The value of the thoracic compliance may be used to assess the user's physiological state. For example, the thoracic compliance of the user may be reduced due to obesity, a chest wall deformity, pleural thickening, and intraperitoneal space-occupying lesion, and the like. Therefore, a pre-set thoracic compliance threshold may be set according to the value of normal thoracic compliance. Once the thoracic compliance of the user exceeds the pre-set thoracic compliance threshold, it indicates that the thoracic compliance of the user is high, or otherwise, it indicates that the thoracic compliance of the user is low. Two first thoracic images may be separately set based on high thoracic compliance and low thoracic compliance. The third pre-set correlation is a correlation between the high thoracic compliance or low thoracic compliance and a differentiation between the two first thoracic images, so that a monitor of a ventilator can determine the value of the thoracic compliance of the user according to a displayed first thoracic image and make appropriate determination.

It may be understood that in this embodiment, the pre-set thoracic compliance threshold may be a value range in addition to a value to provide the determination of the value of the thoracic compliance with a large room.

It should be noted that in this embodiment, when the thoracic compliance of the user is normal, a first thoracic image may be set. The first thoracic image has a differentiation from a corresponding first thoracic image when the thoracic compliance is abnormal to facilitate corresponding determination according to the differentiation. This is not specifically limited herein.

Further, in this embodiment, the displaying a first thoracic image corresponding to the thoracic compliance according to a third pre-set correlation may comprise:

displaying the first thoracic image corresponding to the thoracic compliance according to a correlation between the value of the thoracic compliance and the color of a thoracic contour in the first thoracic image; and/or displaying the first thoracic image corresponding to the thoracic compliance according to a correlation between the value of the thoracic compliance and the thickness of a thoracic contour in the first thoracic image; and/or displaying the first thoracic image corresponding to the thoracic compliance according to a correlation between the value of the thoracic compliance and a second transparency in the first thoracic image.

Specifically, the color of the thoracic contour on the displayed first thoracic image may be used to indicate the value of the thoracic compliance. For example, when the thoracic compliance is high, the color of the thoracic contour on the displayed first thoracic image may be red. When the thoracic compliance is low, the color of the thoracic contour on the displayed first thoracic image may be yellow; and/or the thickness of the thoracic contour on the displayed first thoracic image may be used to indicate the value of the thoracic compliance. For example, when the thoracic compliance is high, the line of the thoracic contour on the displayed first thoracic image may become slightly thinner than that on the original normal thoracic image. When the thoracic compliance is low, the line of the thoracic contour on the displayed first thoracic image may become slightly thicker than that on the original normal thoracic image; and/or the transparency of the displayed first thoracic image may be used to indicate the value of the thoracic compliance. For example, when the thoracic compliance is low, the transparency of the displayed first thoracic image may be less than the transparency of the original normal thoracic image, that is, an adjustment is made to obtain a second transparency, so that different parts on the displayed first thoracic image have more distinct contrast. For example, when the thoracic compliance is high, the transparency of the displayed first thoracic image may be greater than the transparency of the original normal thoracic image, that is, an adjustment is made to obtain another second transparency, so that different parts on the displayed first thoracic image have less distinct contrast. It should be noted that the foregoing content in this embodiment is only an example for description. During actual application, what colors are to be used and how to adjust the thickness or transparency on the first thoracic image for corresponding indication may be designed according to an actual requirement. This is not specifically limited herein.

It may be understood that in addition to the content described above, during actual application, for the third pre-set correlation in this embodiment, other manners may be separately used or used in combination. For example, regardless of the value of the thoracic compliance, when the thoracic compliance is abnormal, a lung contour on the displayed first thoracic image turn orange, and a change in the thickness of the line of the displayed thoracic contour and the transparency is correspondingly combined to indicate the value of the thoracic compliance, provided that the displayed second thoracic image can clearly indicate high or low thoracic compliance. In this case, the thickness of the line of the lung contour on a displayed second lung image may be not obtained by changing the original normal thoracic image. Instead, while there are differentiations in color, as shown in FIG. 7 and FIG. 8 (the color of the thoracic contour in the figures is not shown), the line of the thoracic contour when the thoracic compliance is low may be thicker than the line of the thoracic contour when the thoracic compliance is high. This is not specifically limited herein.

It should be noted that in this embodiment, at least two of ventilation volume, lung compliance, and thoracic compliance of the user may be displayed on a corresponding first image. The states of the ventilation of the user, the lung compliance, and the thoracic compliance may be presented on the same image. That is, the ventilation volume, the lung compliance, and the thoracic compliance are correspondingly indicated on the same image, that is, features of the first lung image, the second lung image, and the first thoracic image are provided. For example, the first thoracic image comprises the second lung image. At least two of the states of ventilation volume, lung compliance, and thoracic compliance of the user may be not presented on the same image. That is, at least two of the first lung image, the second lung image, and the first thoracic image may be separately displayed. This is not specifically limited herein.

In this embodiment, when the first thoracic image comprises the second lung image, the original transparency of the normal lung image may be the same as or different from the original transparency of the normal thoracic image, and when the original degrees of transparency are correspondingly increased or reduced, a degree-of-transparency change range of the normal lung image may be the same as or different from a degree-of-transparency change range of the normal thoracic image. This is not specifically limited herein. For example, the original transparency of the normal lung image and the original transparency of the normal thoracic image may be consistent, and are, for example, a transparency of 80%. When the lung compliance or the thoracic compliance is low, the displayed first lung image may be obtained by reducing the original transparency to the first transparency, and the displayed first thoracic image may be obtained by reducing the original transparency to the second transparency. The first transparency and the second transparency may be the same, for example, a transparency of 65%. In contrast, when the lung compliance or the thoracic compliance is high, a pre-set lung image of the displayed first lung image may be obtained by increasing the original transparency to another first transparency, and the displayed first thoracic image may be obtained by increasing the original transparency to another second transparency. The first transparency and the second transparency may be the same in this case, for example, a transparency of 95%.

It may be understood that for different users, there may further be a state of whether respiration is labored. During a process of providing ventilation therapy to a user, whether respiration is labored may assist a physician or nurse to determine whether the user encounters a special situation, such as sputum suction, or the user has some respiratory diseases and as a result a corresponding respiratory situation occurs. In this case, during a ventilation process, it is particularly important to display a state of whether respiration is labored. Details are described below.

Figure 10:
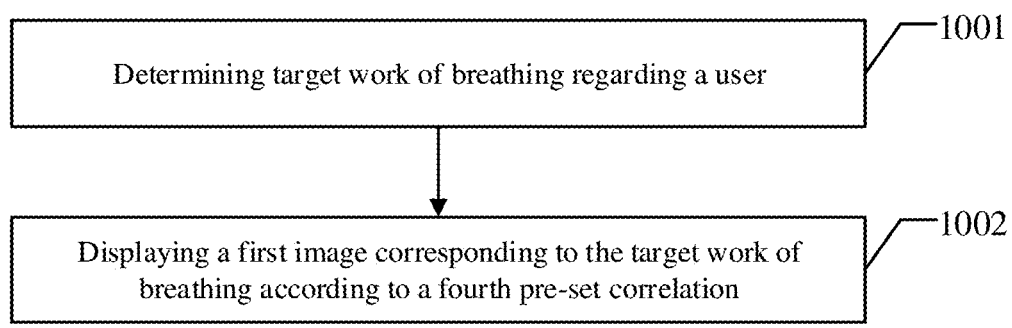
FIG. 10 is a schematic diagram of another embodiment of a method for state display during a ventilation process according to an embodiment of the present disclosure.

Referring to FIG. 10, in certain embodiments of the present disclosure, a method for state display during a ventilation process comprises the following.

1001. The target work of breathing regarding a user is determined.

In this embodiment, during a ventilation process of the user, corresponding monitoring parameter obtained by a corresponding detector may be used to determine the target work of breathing regarding the user. The target work of breathing may at least comprise work of breathing of the user and/or work of breathing of a ventilator.

Specifically, to indicate the target work of breathing in real time, the target work of breathing may be target work of breathing of the user within one respiratory cycle, optionally, and may be target work of breathing of the user during one inhalation process. Generally, three types of usable respiration modes of the ventilator may be defined: spontaneous respiration, assisted respiration or controlled respiration. During spontaneous ventilation without another ventilation mode, a patient breathes in the patient's own rhythm; during assisted ventilation, the patient reduces a baseline pressure to different degrees to start inhalation, and the ventilator may apply a positive pressure to complete respiration to "assist" the patient; and during controlled ventilation, the patient cannot spontaneously breathe or start to breathe and therefore relies on the ventilator to perform each time of respiration. During spontaneous ventilation or assisted ventilation, the patient needs to use respiratory muscles to "do work" to different degrees to breathe. Therefore, the target work of breathing may at least comprise the work of breathing of the user and/or the work of breathing of the ventilator. The work of breathing of the user may be work done by the user to overcome intrapulmonary pressure during an autonomous respiration process. The work of breathing of the ventilator may be work done by the ventilator to overcome air passage pressure during a process of providing ventilation therapy to the user. When the work of breathing is high, it indicates that relatively strong resistance needs to be overcome, and it is relatively labored for the user to breathe or to provide respiratory support for the user. In contrast, it indicates that slightly weak resistance needs to be overcome, and it is relatively easy for the user to breathe or provide respiratory support for the user.

It should be noted that in addition to the target work of breathing within one respiratory cycle described above, the target work of breathing in this embodiment may be, for example, average target work of breathing within a pre-set quantity of previous respiratory cycles, and may be specifically set as required. This is not limited herein.

In this embodiment, for a manner of determining the work of breathing of the user and the work of breathing of the ventilator, reference may be made to the prior art. Details are not described again herein.

1002. A first image corresponding to the target work of breathing is displayed according to a fourth pre-set correlation.

In this embodiment, after the target work of breathing is determined, the first image corresponding to the target work of breathing may be displayed according to the fourth pre-set correlation.

Specifically, the fourth pre-set correlation regarding the target work of breathing may be prestored according to the value of the target work of breathing. The value of the target work of breathing may be used to facilitate understanding of pathological and physiological processes of the user's disease, determine the severity of the disease, therapeutic response, whether the patient can be safely taken off the ventilator, and the like. If the target work of breathing is relatively high, the user may have a disease that results in relatively labored respiration, for example, the user's trachea is compressed. Therefore, a pre-set work of breathing threshold may be set according to the values of normal work of breathing of the user and normal work of breathing of the ventilator. Once the target work of breathing exceeds the pre-set work of breathing threshold, it indicates that the target work of breathing is high, and it is relatively labored for the user to breathe or provide respiratory support for the user, or otherwise, it indicates that the target work of breathing is low. The low target work of breathing is relatively close to the normal work of breathing. During actual application, because the user and the ventilator generate work of breathing in a normal state, if the target work of breathing is not the normal work of breathing, the target work of breathing is definitely greater than the normal work of breathing (that is, the case in which the target work of breathing is high) or close to the normal work of breathing (that is, the case in which the target work of breathing is low). Based on the high target work of breathing and the low target work of breathing, a correlation of the output display corresponding to the first image may be set. The fourth pre-set correlation is a correlation between the high or low target work of breathing and an output display corresponding to the first image, so that a monitor of the ventilator can determine the value of the target work of breathing according to a display pattern of the displayed first image and make appropriate determination.

It should be noted that in this embodiment, when the target work of breathing is closer to the normal work of breathing, an output display pattern of the first image is closer to an output display pattern of the first image corresponding to the normal work of breathing.

Further, in this embodiment, the displaying a first image corresponding to the target work of breathing according to a fourth pre-set correlation may comprise:

displaying the first image according output smoothness corresponding to the value of the target work of breathing, the output smoothness being inversely correlated to the value of the target work of breathing; and/or differentially displaying the first image in adjacent frames according to the value of the target work of breathing, the degree of differentiation is positively correlated to the value of the target work of breathing.

Specifically, the output smoothness of the first image may be used to indicate the value of the target work of breathing. For example, it is assumed that when the work of breathing is normal, within one respiratory cycle, the first image may output 10 frames of image and the output is relatively smooth. Switching between adjacent frames of image may be imperceptible to naked eyes. The presentation seems to be static presentation. However, when the target work of breathing is high, it is possible that only 5 frames can be output within the same respiratory cycle, and the output display of the first image may be not smooth. Switching between adjacent frames of image is perceptible, and the presentation appears to be dynamic presentation. The output smoothness of the first image may be inversely correlated to the value of the target work of breathing. That is, when the target work of breathing decreases, the output display of the first image becomes increasingly smooth; and/or a differentiation on the first image between adjacent frames may be used to indicate the value of the target work of breathing. For example, it is assumed that when the work of breathing is normal, within one respiratory cycle, the first image may be output according to 10 frames of image, and the output of the 10 frames of image may be used for the dynamic presentation of inhalation and exhalation. Because an inhalation state and an exhalation state are inconsistent, dynamic presentation of inhalation and dynamic presentation of exhalation on the 10 frames of image are inconsistent. Therefore, when the target work of breathing is high, it is possible that only 5 frames can be output within the same respiratory cycle, and the degree of the differentiation between adjacent frames of the first image may be relatively large. For example, the original display of inhalation corresponds to state 1, state 2, state 3, state 4 and state 5, but after the state 1 is displayed, the first image corresponding to the state 4 may be directly output and displayed, and the degree of the differentiation is positively correlated to the value of the target work of breathing. That is, when the target work of breathing decreases, the differentiation on the displayed first image between adjacent frames is increasingly small. That is, after the state 1 is displayed, the first image corresponding to the state 3 may be output and displayed. It should be noted that the foregoing content in this embodiment is only an example for description. During actual application, how to use the output smoothness of the first image and the differentiation between adjacent frames of the first image for corresponding indication may be designed according to an actual requirement. This is not specifically limited herein.

It may be understood that in addition to the content described above, during actual application, for the fourth pre-set correlation in this embodiment, other manners may be separately used or used in combination, provided that the pre-set lung image can clearly indicate the value of the target work of breathing. This is not specifically limited herein.

It should be noted that in this embodiment, at least two of ventilation volume, lung compliance, thoracic compliance, and the target work of breathing may be displayed on a corresponding first image. The ventilation volume, the lung compliance, and the thoracic compliance may be correspondingly indicated on the same image, that is, features of a first lung image, a second lung image, and a first thoracic image are provided. For example, the first thoracic image comprises the second lung image, and corresponding output processing may be performed on the same image to indicate the target work of breathing. The states of at least two of the ventilation volume, the lung compliance, the thoracic compliance, and the target work of breathing may be not presented on the same image. That is, at least two of the first lung image, the second lung image, and the first thoracic image may be separate from each other. The target work of breathing may be or may not be indicated on any one of the first lung image, the second lung image, and the first thoracic image. This is not specifically limited herein.

Further, during a ventilation process of the user, regardless of a ventilation mode of the ventilator, the user may have an inhalation state and an exhalation state. A change caused by a respiration state is displayed on a pre-set lung image, so that a monitor of the ventilator can intuitively determine a current respiration state of the user, for example, whether the user is in an inhalation state or an exhalation state, thereby enhancing a display function of a device for state display during a ventilation process and helping improve use experience. Such a case is specifically described below.

Figure 11:
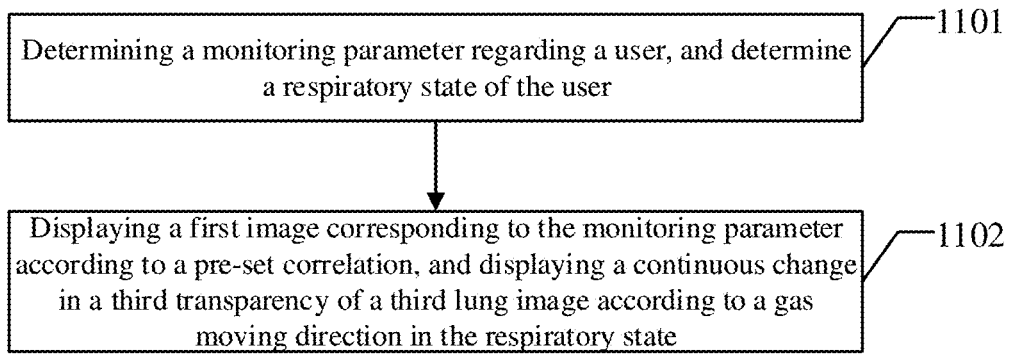
FIG. 11 is a schematic diagram of another embodiment of a method for state display during a ventilation process according to an embodiment of the present disclosure.

Referring to FIG. 11, in certain embodiments of the present disclosure, another embodiment of a method for state display during a ventilation process comprises the following.

1101. A monitoring parameter regarding a user is determined, and a respiration state of the user is determined.

In this embodiment, during a ventilation process of the user, corresponding monitoring parameter obtained by using a corresponding detector may be used to determine the monitoring parameter regarding the user and determine the respiration state of the user. The respiration state may comprise an inhalation state and an exhalation state.

In this embodiment, for corresponding content of determining the monitoring parameter regarding the user, reference may be made to the content described in step 101 in the embodiment shown in FIG. 1. Details are not described again herein.

Specifically, to intuitively present the respiration state of the user in real time, the respiration state may be a current respiration state of the user, that is, an inhalation state in the case of inhalation and an exhalation state in the case of exhalation. Therefore, optionally, because of the specific characteristics of ventilation volume, lung compliance, thoracic compliance, and target work of breathing of the user, the ventilation volume, the lung compliance, the thoracic compliance, and the target work of breathing of the user may be a detection result within the last respiratory cycle, and the respiration state of the user may be a real-time detection result within a current respiratory cycle.

For example, air passage pressure or the like may be used to determine the respiration state of the user. The air passage pressure is pressure in an air passage of a ventilator. When the user inhales, the pressure in the air passage of the ventilator reduces. When the user exhales, the pressure in the air passage of the ventilator increases.

It may be understood that in this embodiment, in addition to the foregoing use of air passage pressure to determine the respiration state of the user, during actual application, another manner may be used provided that the respiration state of the user can be determined. For details, reference may be made to the prior art. Details are not described again herein. This is not specifically limited herein.

1102. A first image corresponding to the monitoring parameter is displayed according to a pre-set correlation, and a continuous change in a third transparency of a third lung image is displayed according to a gas moving direction in the respiration state.

In this embodiment, after the monitoring parameter regarding the user and the respiration state of the user are determined, the first image corresponding to the monitoring parameter may be displayed according to the pre-set correlation, the continuous change in the third transparency of the third lung image may further be displayed according to a gas moving direction in the respiration state.

In this embodiment, for corresponding content of displaying the first image corresponding to the monitoring parameter according to the pre-set correlation, reference may be made to the content described in step 102 in the embodiment shown in FIG. 1. Details are not described again herein.

In this embodiment, an example in which the monitoring parameter is a detection result within the previous respiratory cycle of the current respiratory cycle and the respiration state of the user is a real-time detection result within the current respiratory cycle is used for description.

Specifically, when the user inhales, gas may enter the lung from outside the body through the trachea. When the user exhales, gas may be discharged outside the body from the lung through the trachea. Therefore, it can be known that both gas that enters the body and gas that is discharged outside the body have corresponding displacements according to different respiration states of the user. In comparison, when gas is inhaled into the lung, a change in light and shadow caused by gas may gradually occupy the lung image as the gas displaces, to gradually affect the clarity of the lung. When gas is exhaled outside the body, a change in light and shadow caused by the gas may gradually leave the lung image as the gas displaces, to gradually restore the clarity of the lung. Therefore, in this embodiment, the continuous change in the transparency may be used to indicate a displacement change in light and shadow caused by gas, to visually and vividly reflect the respiration state of the user, so that a continuous change in a third transparency of the pre-set lung image may be displayed according to a gas moving direction in the respiration state.

Figure 12:
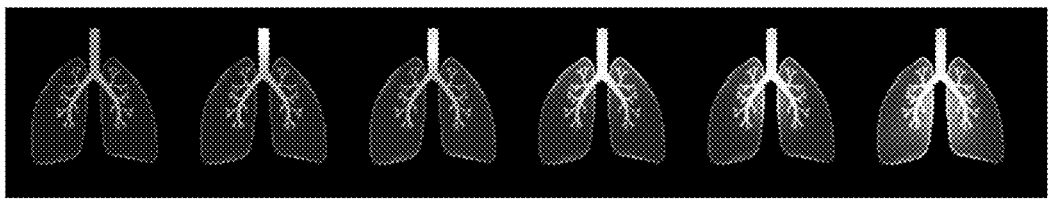
FIG. 12 is a schematic diagram of image display during an inhalation process according to an embodiment of the present disclosure.
Figure 13:
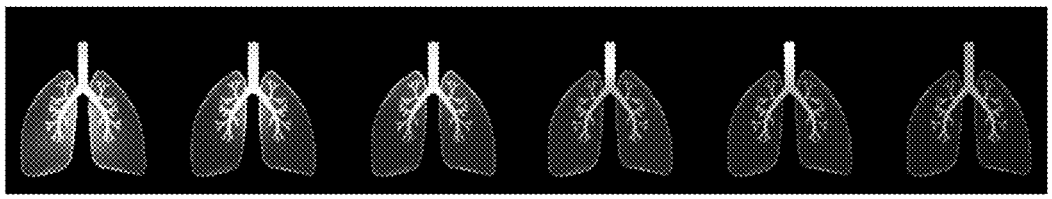
FIG. 13 is a schematic diagram of image display during an exhalation process according to an embodiment of the present disclosure.

For example, when the user inhales, as shown in FIG. 12, gas slowly enters the left and right bronchi of the lung through the trachea. Therefore, as gas moves inward, on the third lung image, a transparency of the gas from trachea to the left and right bronchi may be gradually increased to the third transparency. When the user exhales, as shown in FIG. 13, gas is slowly discharged outside the body from the lung. Therefore, as gas moves outward, on the third lung image, a transparency of gas from the left and right bronchi to the trachea may be gradually increased to the third transparency. When the user inhales and exhales, change directions of the third transparency of the third lung image are opposite, so that an intuitive change direction of the third transparency of the third lung image may be used to determine whether the user is inhaling or exhaling.

It should be noted that in this embodiment, at least two of the ventilation volume, the lung compliance, the thoracic compliance, the target work of breathing, and the respiration state may be displayed on a corresponding first image. The ventilation volume, the lung compliance, the thoracic compliance, and the respiration state may be correspondingly indicated on the same image, that is, features of a first lung image, a second lung image, a first thoracic image, and the third lung image are provided. For example, the first thoracic image comprises the second lung image, and corresponding output processing may be performed on the same image to indicate the target work of breathing. The states of at least two of the ventilation volume, the lung compliance, the thoracic compliance, the target work of breathing, and the respiration state may be not presented on the same image. That is, at least two of the first lung image, the second lung image, the first thoracic image, and the third lung image may be independent of each other. The target work of breathing may be or may not be indicated on any one of the first lung image, the second lung image, the first thoracic image, and the third lung image. This is not specifically limited herein.

Figure 14:
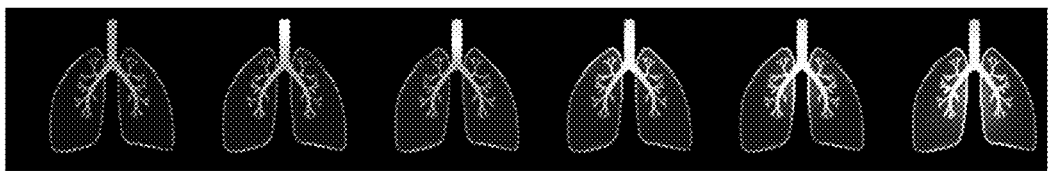
FIG. 14 is a schematic diagram of image display when the ventilation volume is normal and the lung compliance is low during an inhalation process according to an embodiment of the present disclosure.
Figure 15:
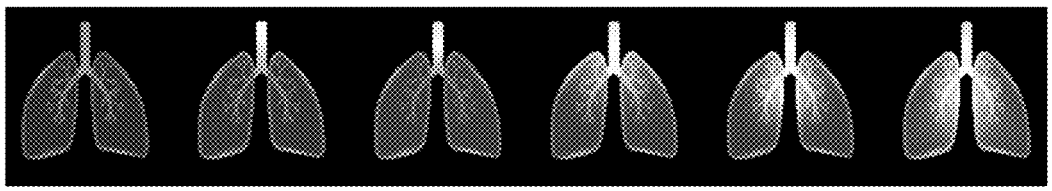
FIG. 15 is a schematic diagram of image display when the ventilation volume is normal and the lung compliance is high during an exhalation process according to an embodiment of the present disclosure.

For example, after the ventilation volume, the lung compliance, and the respiration state of the user are determined, changes corresponding to the ventilation volume, the lung compliance, and the respiration state may be displayed. As shown in FIG. 14, the ventilation volume of the user is normal, the lung compliance of the user is low, and the user is currently in an inhalation state. As shown in FIG. 15, the ventilation volume of the user is normal, the lung compliance of the user is high, and the user is currently in an inhalation state.

Based on the foregoing description, when the respiration state and any of the ventilation volume, the lung compliance, the thoracic compliance, and the target work of breathing are correspondingly indicated, during actual application, for determination of the respiration state and any of the ventilation volume, the lung compliance, the thoracic compliance, and the target work of breathing of the user within a corresponding respiratory cycle, in addition to the content described in the foregoing embodiment, during actual application, another setting may be used according to an actual requirement. For example, for the synchronicity between the respiration state and any of the ventilation volume, the lung compliance, the thoracic compliance, and the target work of breathing of the user, the respiration state and any of the ventilation volume, the lung compliance, the thoracic compliance, and the target work of breathing of the user may be a detection result within the previous respiratory cycle of the current respiratory cycle. That is, the respiration state and any of the ventilation volume, the lung compliance, the thoracic compliance, and the target work of breathing regarding the user within one respiratory cycle before a current time are presented. This is not specifically limited herein.

In this embodiment, when the first lung image is the same as the third lung image, that is, corresponding features of the first lung image and the third lung image are provided on the same image, because there are changes in a transparency on the corresponding lung image in both the case of abnormal lung compliance and the indication of the respiration state, to avoid confusion of the two states, the first transparency of the first lung image is different from the third transparency of the third lung image. For example, the original transparency of the normal lung image is 80%. When the lung compliance is low, a displayed first lung image may be reduced from the original transparency to the first transparency, for example, a transparency of 65%, or otherwise, when the lung compliance is high, a pre-set lung image of the displayed first lung image may be increased from the original transparency to another first transparency, for example, a transparency of 95%. However, according to the respiration state of the user, the third lung image may be gradually increased according to a gas moving direction in the respiration state from the original transparency to the third transparency, for example, a transparency of 90%, which is therefore differentiated from the first transparency.

Further, based on the embodiment described above, during actual application, monitoring data of at least one of the ventilation volume, the lung compliance, the thoracic compliance, and the work of breathing, especially, monitoring data within the previous respiratory cycle of the current respiratory cycle, and/or a data change trend of the monitoring data within a pre-set time period before a current time, may be output according to a pre-set rule.

For example, for the ventilation volume, in addition to the indication of the value of the ventilation volume on the first lung image, the real-time value of the ventilation volume may be output to provide a specific value, to facilitate direct determination of the ventilation volume of the user by a monitor of the ventilator. For the reason of calculating the ventilation volume, relative to the current time, the output real-time value may be the ventilation volume within the previous respiratory cycle of the current respiratory cycle. During actual application, minute ventilation volume at the current time may be output, to provide the monitor of the ventilator with more reference information. Moreover, to assist a physician to determine a change trend of the user's lung ventilation and assist the physician to assess a therapeutic effect, a data change trend of the ventilation volume within the pre-set time period before the current time may be output. For example, a line chart of the values of end-tidal carbon dioxide within each respiratory cycle within the last 30 minutes may be displayed, so that a change trend of ventilation volume of the user within the last 30 minutes can be indicated according to a change trend of the end-tidal carbon dioxide within the last 30 minutes.

For another example, the target work of breathing comprises work of breathing of the user and work of breathing of the ventilator for description. During actual application, the real-time value of the target work of breathing may further be output to provide a specific value, to facilitate direct determination of the work of breathing of the user by the monitor of the ventilator and assist in excluding undesirable output smoothness caused by a software or hardware fault when the target work of breathing or the like causes undesirable output smoothness of the first image. For the reason of calculating the target work of breathing, relative to the current time, the output real-time value may be the target work of breathing within the previous respiratory cycle of the current respiratory cycle, and the work of breathing of the user and the work of breathing of the ventilator may be separately provided. The real-time value of the target work of breathing may be indicated by a value or may be indicated by a graph such as a bar chart. During actual application, to assist a physician to determine a change trend of the target work of breathing, a data change trend of the target work of breathing within the pre-set time period before a current time may further be output. For example, the value of the target work of breathing within each respiratory cycle within the last 30 minutes may be displayed on a bar chart. For the bar chart, a rectangular bar may indicate the target work of breathing measured within one respiratory cycle. Moreover, the rectangular bar may be divided into two segments. One segment indicates the work of breathing of the user, and the other segment indicates the work of breathing of the ventilator. The work of breathing of the user and the work of breathing of the ventilator may be differentiated by a segmentation line or may be differentiated by different colors, so that the obtained bar chart can indicate a change trend of the target work of breathing within the last 30 minutes and can show change trends of the work of breathing of the user and the work of breathing of the ventilator within the last 30 minutes.

It should be noted that in this embodiment, a display form of a data change trend of at least one of the ventilation volume, the lung compliance, the thoracic compliance, and the work of breathing within the pre-set time period before the current time is only an example for description in the foregoing content. During actual application, display information (comprising a color, a format, a graph type, a table form, and the like) in the display form and what reference data is used to display a short trend of corresponding monitoring data may be set according to an actual requirement. This is not specifically limited herein.

Furthermore, based on the content described above, during actual application, during output of monitoring data of at least one of the ventilation volume, the lung compliance, the thoracic compliance, and the work of breathing within the previous respiratory cycle of the current respiratory cycle, when monitoring data corresponding to one of the ventilation volume, the lung compliance, the thoracic compliance, and the work of breathing is abnormal, the monitoring data may further be highlighted to make the monitor of the ventilator more alert to an abnormality.

A manner of highlighting monitoring data may comprise, but is not limited to, highlighting with a color, highlighting with a font size, and highlighting with a pre-set shape.

Figure 16:
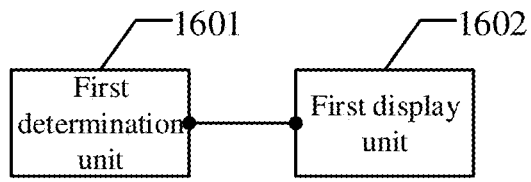
FIG. 16 is a schematic diagram of an embodiment of a device for state display during a ventilation process according to an embodiment of the present disclosure.

The method for state display during a ventilation process in certain embodiments of the present disclosure is described above. A device for state display during a ventilation process in certain embodiments of the present disclosure is described below. Referring to FIG. 16, an embodiment of a device for state display during a ventilation process according to an embodiment of the present disclosure comprises:

a first determination unit 1601 configured for determining a monitoring parameter regarding a user; and a first display unit 1602 configured for displaying a first image corresponding to the monitoring parameter according to a pre-set correlation. The first determination unit 1601 can be implemented by one or more processor, one or more memory, and one or more computer program. The first display unit 1602 may be implemented by one or more computer displays, such as a light emitting diode (LED) monitor or cathode ray tube (CRT) monitor.

In this embodiment, during a ventilation process of a user, the first determination unit 1601 determines a monitoring parameter regarding the user, and the first display unit 1602 may display a first image corresponding to the monitoring parameter according to a pre-set correlation, so as to provide a physician or nurse monitoring a ventilator with intuitive image display of a ventilation state during the ventilation process of the user and improve the accurate determination of the ventilation state of the user by the physician or nurse, thereby facilitating timely adjustment of a respiratory therapy strategy and helping improve ventilator-based treatment experience for the user.

Optionally, in some embodiments of the present disclosure, when the monitoring parameter is ventilation volume, the first image comprises a first lung image; and the first display unit 1602 may further be specifically configured for:

displaying the first lung image corresponding to the ventilation volume according to a correlation between the value of the ventilation volume and the position of a pre-set plot in the first lung image.

Optionally, in some embodiments of the present disclosure, when the monitoring parameter comprises lung compliance, the first image comprises a second lung image; and the first display unit 1602 may further be specifically configured for:

displaying the second lung image corresponding to the lung compliance according to a correlation between the value of the lung compliance and the color of a lung contour in the second lung image; and/or displaying the second lung image corresponding to the lung compliance according to a correlation between the value of the lung compliance and the thickness of a lung contour in the second lung image; and/or displaying the second lung image corresponding to the lung compliance according to a correlation between the value of the lung compliance and a first transparency of a second lung image;

the size of the second lung image is remained unchanged.

Optionally, in some embodiments of the present disclosure, when the monitoring parameter comprises thoracic compliance, the first image comprises a first thoracic image; and the first display unit 1602 may further be specifically configured for:

displaying the first thoracic image corresponding to the thoracic compliance according to a correlation between the value of the thoracic compliance and the color of a thoracic contour in the first thoracic image; and/or displaying the first thoracic image corresponding to the thoracic compliance according to a correlation between the value of the thoracic compliance and the thickness of a thoracic contour in the first thoracic image; and/or displaying the first thoracic image corresponding to the thoracic compliance according to a correlation between the value of the thoracic compliance and a second transparency in the first thoracic image.

Optionally, in some embodiments of the present disclosure, when the monitoring parameter comprises target work of breathing, the first display unit 1602 may further be specifically configured for:

displaying the first image according output smoothness corresponding to the value of the target work of breathing, the output smoothness being inversely correlated to the value of the target work of breathing; and/or differentially displaying the first image in adjacent frames according to the value of the target work of breathing, the degree of differentiation is positively correlated to the value of the target work of breathing.

Figure 17:
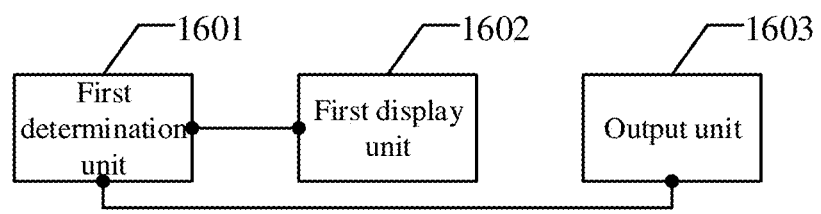
FIG. 17 is a schematic diagram of another embodiment of a device for state display during a ventilation process according to an embodiment of the present disclosure.

Optionally, in some embodiments of the present disclosure, referring to FIG. 17, the device may further comprise:

an output unit 1603 configured for outputting, according to a pre-set rule, monitoring data of at least one of the ventilation volume, the lung compliance, the thoracic compliance and the target work of breathing and/or the trend of changes in data within a pre-set time period before the current time. The output unit 1603 may be implemented as an output interface, such as a network interface or a serial or parallel port.

Figure 18:
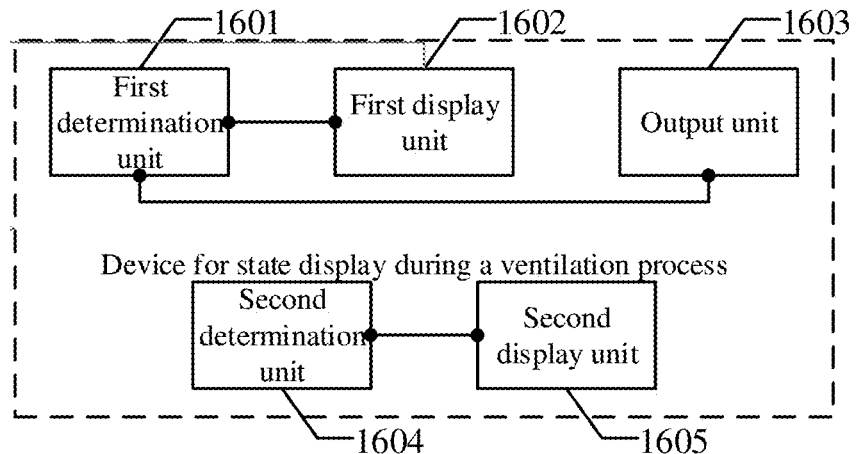
FIG. 18 is a schematic diagram of another embodiment of a device for state display during a ventilation process according to an embodiment of the present disclosure.

Optionally, in some embodiments of the present disclosure, referring to FIG. 18, the device may further comprise:

a second determination unit 1604 configured for determining a respiration state of the user, the respiration state comprising an exhalation state and an inhalation state; and a second display unit 1605 configured for displaying a continuous change in a third transparency of a third lung image according to a gas moving direction in the respiration state;

the size of the third lung image is remained unchanged. The second determination unit 1604 can be implemented by one or more processor, one or more memory, and one or more computer program. The second display unit 1605 may be implemented by one or more computer displays, such as a light emitting diode (LED) monitor or cathode ray tube (CRT) monitor. The second determination unit 1604 can be the same physical device as the first determination unit 1601. The second display unit 1605 may be the same physical device as the first display unit 1602.

Correspondingly, the present disclosure further provides a ventilator. The ventilator may at least comprise the device for state display during a ventilation process described above. For more details, reference may be made together to the description in the foregoing embodiments.

Figure 19:
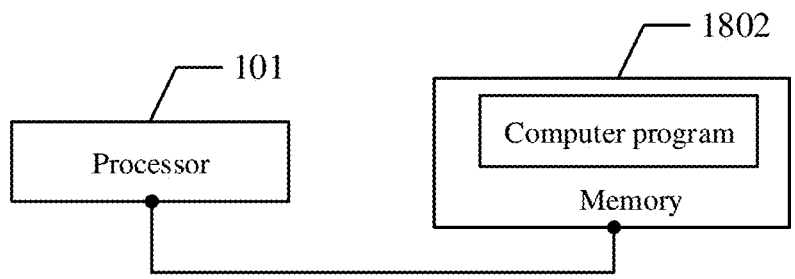
FIG. 19 is a schematic diagram of an embodiment of a computer device according to an embodiment of the present disclosure.

The device for state display during a ventilation process in certain embodiments of the present disclosure is described above from the perspective of modular functional entities. The computer device in certain embodiments of the present disclosure is described below from the perspective of hardware processing:

Referring to FIG. 19, an embodiment of a computer device according to an embodiment of the present disclosure comprises:

a processor 1901 and a memory 1902, wherein the memory 1902 is configured for storing a computer program, the processor 1901 is configured for executing the computer program stored in the memory 1902 to implement the following:

determining a monitoring parameter regarding a user; and displaying a first image corresponding to the monitoring parameter according to a pre-set correlation.

In some embodiments of the present disclosure, when the monitoring parameter is ventilation volume, the first image comprises a first lung image, and the processor 1901 may further be configured for implementing the following:

the s displaying of the first image corresponding to the monitoring parameter according to a pre-set correlation comprises:

displaying the first lung image corresponding to the ventilation volume according to a correlation between the value of the ventilation volume and the position of a pre-set plot in the first lung image.

In some embodiments of the present disclosure, when the monitoring parameter comprises lung compliance, the first image comprises a second lung image, and the processor 1901 may further be configured for implementing the following:

displaying the second lung image corresponding to the lung compliance according to a correlation between the value of the lung compliance and the color of a lung contour in the second lung image; and/or displaying the second lung image corresponding to the lung compliance according to a correlation between the value of the lung compliance and the thickness of a lung contour in the second lung image; and/or displaying the second lung image corresponding to the lung compliance according to a correlation between the value of the lung compliance and a first transparency of a second lung image;

the size of the second lung image is remained unchanged.

In some embodiments of the present disclosure, when the monitoring parameter comprises thoracic compliance, the first image comprises a first thoracic image, and the processor 1901 may further be configured for implementing the following:

displaying the first thoracic image corresponding to the thoracic compliance according to a correlation between the value of the thoracic compliance and the color of a thoracic contour in the first thoracic image; and/or displaying the first thoracic image corresponding to the thoracic compliance according to a correlation between the value of the thoracic compliance and the thickness of a thoracic contour in the first thoracic image; and/or displaying the first thoracic image corresponding to the thoracic compliance according to a correlation between the value of the thoracic compliance and a second transparency in the first thoracic image.

In some embodiments of the present disclosure, when the monitoring parameter comprises target work of breathing, the processor 1901 may further be configured for implementing the following:

displaying the first image according output smoothness corresponding to the value of the target work of breathing, the output smoothness being inversely correlated to the value of the target work of breathing; and/or differentially displaying the first image in adjacent frames according to the value of the target work of breathing, the degree of differentiation is positively correlated to the value of the target work of breathing.

In some embodiments of the present disclosure, the processor 1901 may further be configured for implementing the following:

outputting, according to a pre-set rule, monitoring data of at least one of the ventilation volume, the lung compliance, the thoracic compliance and the target work of breathing and/or the trend of changes in data within a pre-set time period before the current time.

In some embodiments of the present disclosure, the processor 1901 may further be configured for implementing the following:

determining a respiration state of the user, the respiration state comprising an exhalation state and an inhalation state; and displaying a continuous change in a third transparency of a third lung image according to a gas moving direction in the respiration state;

the size of the third lung image is remained unchanged.

It may be understood that the processor in the foregoing computer device may execute the computer program to implement the functions of the units in the foregoing corresponding device embodiments. Details are not described herein again. For example, the computer program may be divided into one or more modules/units. The one or more modules/units are stored in the memory and are executed by the processor to complete various methods or processes disclosed herein. The one or more modules/units may be a series of computer program instruction segments that can implement specific functions. The instruction segment is used to describe an execution process of the computer program in the device for state display during a ventilation process. For example, the computer program may be divided into units in the device for state display during a ventilation process. The units may implement specific functions described in the foregoing corresponding device for state display during a ventilation process.

The compute device may be a computing device such as a desktop computer, a notebook, a palmtop computer, and a cloud server. The computer device may include, but is not limited to, a processor, and a memory. A person skilled in the art may understand that the processor and the memory are merely examples of the computer device, but do not constitute a limitation to the computer device. More or fewer components may be comprised, some components may be combined, or different components may be comprised. For example, the computer device may further comprise an input/output device, a network access device, a bus, and the like.

The processor may be a central processing unit (CPU) or another general-purpose processor, a digital signal processor (DSP), an application-specific integrated circuit (ASIC), a field programmable gate array (FPGA) or another programmable logical device, a discrete gate or transistor logic device, a discrete hardware component or the like. The general-purpose processor may be a microprocessor, or the processor may be any conventional processor or the like. The processor is a control center of the computer device, and is connected to various parts of the computer device by various interfaces and lines.

The memory may be configured for storing the computer program and/or module. The processor runs or executes the computer program and/or module stored in the memory and invokes data stored in the memory to implement various functions of the computer device. The memory may mainly comprise a program storage area and a data storage area. The program storage area may store an operating system, an application program required for at least one function, and the like; and the data storage area may store data created according to the use of a terminal and the like. In addition, the memory may include a high-speed random access memory (RAM), and may further include a non-volatile memory such as a hard disk, an internal memory, and a removable hard disk, a smart media card (SMC), a secure digital (sensed by) card, a flash card, at least one disk storage device, a flash device or another volatile solid-state storage device.

The present disclosure further provides a computer-readable storage medium, the computer-readable storage medium storing a computer program, the computer program is executed by a processor to implement the following:

determining a monitoring parameter regarding a user; and
displaying a first image corresponding to the monitoring parameter according to a pre-set correlation.

In some embodiments of the present disclosure, when the monitoring parameter is ventilation volume, the first image comprises a first lung image, and the computer program stored in the computer-readable storage medium is executed by the processor to further implement the following:

the displaying of the first image corresponding to the monitoring parameter according to a pre-set correlation comprises:

displaying the first lung image corresponding to the ventilation volume according to a correlation between the value of the ventilation volume and the position of a pre-set plot in the first lung image.

In some embodiments of the present disclosure, when the monitoring parameter comprises lung compliance, the first image comprises a second lung image, and the computer program stored in the computer-readable storage medium is executed by the processor to further implement the following:

displaying the second lung image corresponding to the lung compliance according to a correlation between the value of the lung compliance and the color of a lung contour in the second lung image; and/or displaying the second lung image corresponding to the lung compliance according to a correlation between the value of the lung compliance and the thickness of a lung contour in the second lung image; and/or displaying the second lung image corresponding to the lung compliance according to a correlation between the value of the lung compliance and a first transparency of a second lung image;

the size of the second lung image is remained unchanged.

In some embodiments of the present disclosure, when the monitoring parameter comprises thoracic compliance, the first image comprises a first thoracic image, and the computer program stored in the computer-readable storage medium is executed by the processor to further implement the following:

displaying the first thoracic image corresponding to the thoracic compliance according to a correlation between the value of the thoracic compliance and the color of a thoracic contour in the first thoracic image; and/or displaying the first thoracic image corresponding to the thoracic compliance according to a correlation between the value of the thoracic compliance and the thickness of a thoracic contour in the first thoracic image; and/or displaying the first thoracic image corresponding to the thoracic compliance according to a correlation between the value of the thoracic compliance and a second transparency in the first thoracic image.

In some embodiments of the present disclosure, when the monitoring parameter comprises target work of breathing, the computer program stored in the computer-readable storage medium is executed by the processor to further implement the following:

displaying the first image according output smoothness corresponding to the value of the target work of breathing, the output smoothness being inversely correlated to the value of the target work of breathing; and/or differentially displaying the first image in adjacent frames according to the value of the target work of breathing, the degree of differentiation is positively correlated to the value of the target work of breathing.

In some embodiments of the present disclosure, the computer program stored in the computer-readable storage medium is executed by the processor to further implement the following:

outputting, according to a pre-set rule, monitoring data of at least one of the ventilation volume, the lung compliance, the thoracic compliance and the target work of breathing and/or the trend of changes in data within a pre-set time period before the current time.

In some embodiments of the present disclosure, the computer program stored in the computer-readable storage medium is executed by the processor to further implement the following:

determining a respiration state of the user, the respiration state comprising an exhalation state and an inhalation state; and displaying a continuous change in a third transparency of a third lung image according to a gas moving direction in the respiration state;

the size of the third lung image is remained unchanged.

It may be understood that if the integrated unit is implemented in the form of a software function unit and sold or used as an independent product, it may be stored in a corresponding computer readable storage medium. Based on such an understanding, all or some procedures in the methods in the corresponding embodiments implemented in accordance with the present disclosure may be accomplished by a computer program instructing related hardware. The computer program may be stored in one computer-readable storage medium. The computer program is executed by a processor to implement the steps in the method embodiments. The computer program comprises computer program code, which may be in the form of source code, object code, an executable file or some intermediate form, etc. The computer-readable medium may include: any entity or device capable of carrying the computer program code, such as a recording medium, a USB flash drive, a mobile hard disk drive, a magnetic disk, a compact disk, a computer memory, a read-only memory (ROM), a RAM, an electrical carrier signal, a telecommunication signal and a software distribution medium. It should be noted that appropriate additions or deletions may be made to the content comprised in the computer-readable medium according to the requirements of the legislation in a jurisdictional area and patent practice. For example, in some jurisdictional areas, according to the legislation and patent practice, the computer-readable medium does not include an electrical carrier signal and a telecommunication signal.

Those skilled in the art can clearly understand that for convenience and conciseness of description, the specific working processes of the above-described systems, devices and units can refer to the corresponding processes in the above-described embodiments of the method and will not be further described here.

In several embodiments provided in this application, it is to be understood that the disclosed systems, devices and methods may be implemented in other ways. For example, the apparatus embodiments described above are merely exemplary. For example, the division of the units is only a logic function division. In actual implementation, there may be other division methods, for example, multiple units or assemblies may be combined or integrated into another system, or some features may be omitted or not implemented. In a further aspect, the mutual coupling or direct coupling or communication connection shown or discussed may be indirect coupling or communication connection through some interfaces, devices or units, and may be in electrical, mechanical or other forms.

The units described as separate parts may or may not be physically separated, and the parts displayed as units may or may not be physical units, i.e., may be located in one place or may be distributed over multiple network units. Some or all of the units can be selected according to actual needs to achieve the purpose of the present embodiment.

In addition, the functional units in various embodiments of the present disclosure may be integrated into one processing unit or may alternatively exist as being physically separate, or two or more of the units may be integrated into one unit.

As described above, the above embodiments are only for the purpose of illustration of the technical solution of the present disclosure and not limitation; and although principles of the present disclosure have been described in detail with reference to the foregoing embodiments, it should be understood by those of ordinary skill in the art that modifications can still be made to the technical solution described in the foregoing embodiments or equivalent substitutions of some technical features thereof is also possible, while these modifications or substitutions do not make the essence of the corresponding technical solution depart from the spirit and scope of the technical solutions of the described embodiments of the present disclosure.

The invention claimed is:

1. A method for state display during a ventilation process, comprising:
   determining, by a processor, a monitoring parameter regarding a user;
   determining a respiration state of the user, the respiration state comprising an exhalation state and an inhalation state; and
   displaying a plurality of images, corresponding to the monitoring parameter, according to a pre-set correlation, to facilitate timely adjustment of a therapy strategy applied to the user, wherein displaying the plurality of images further comprises:
      in response to the monitoring parameter comprising a first monitoring parameter, displaying a continuous change in a first transparency of the plurality of images according to the respiration state and the first monitoring parameter, the continuous change in the first transparency being configured to enable determination of whether the respiration state is an exhalation state or an inhalation state; and
      in response to the monitoring parameter comprising a second monitoring parameter, displaying a continuous change in a second transparency of the plurality of images according to the respiration state and the second monitoring parameter, the continuous change in the second transparency being different from the continuous change in the first transparency.

2. The method of claim 1, wherein the monitoring parameter comprises at least one of ventilation volume, lung compliance, thoracic compliance, or target work of breathing; and
   the target work of breathing comprises at least one of work of breathing of the user or work of breathing of a ventilator.

3. The method of claim 2, wherein the plurality of images comprise a first lung image, and the monitoring parameter comprises the ventilation volume, and
   wherein the displaying of the plurality of images, corresponding to the monitoring parameter, according to the pre-set correlation comprises:

displaying the first lung image corresponding to the ventilation volume according to a correlation between a value of the ventilation volume and a position of a pre-set plot in the first lung image.

4. The method of claim 2, wherein the monitoring parameter comprises the lung compliance, and the plurality of images comprise a second lung image, and
wherein the displaying of the plurality of images, corresponding to the monitoring parameter, according to the pre-set correlation comprises at least one of:
displaying the second lung image corresponding to the lung compliance according to a correlation between a value of the lung compliance and a color of a lung contour in the second lung image;
displaying the second lung image corresponding to the lung compliance according to a correlation between a value of the lung compliance and a thickness of the lung contour in the second lung image; or
displaying the second lung image corresponding to the lung compliance according to a correlation between a value of the lung compliance and a third transparency of the second lung image,
wherein sizes of the plurality of images that comprise the second lung image remain unchanged.

5. The method of claim 2, wherein the monitoring parameter comprises the thoracic compliance, and the plurality of images comprise a first thoracic image; and
wherein the displaying of the plurality of images, corresponding to the monitoring parameter, according to the pre-set correlation comprises at least one of:
displaying the first thoracic image corresponding to the thoracic compliance according to a correlation between a value of the thoracic compliance and a color of a thoracic contour in the first thoracic image;
displaying the first thoracic image corresponding to the thoracic compliance according to a correlation between a value of the thoracic compliance and a thickness of the thoracic contour in the first thoracic image; or
displaying the first thoracic image corresponding to the thoracic compliance according to a correlation between a value of the thoracic compliance and a fourth transparency in the first thoracic image.

6. The method of claim 2, wherein the monitoring parameter comprises the target work of breathing, and
wherein the displaying of the plurality of images, corresponding to the monitoring parameter, according to the pre-set correlation comprises at least one of:
displaying the plurality of images according to output smoothness which is inversely correlated to a value of the target work of breathing; or
differentially displaying the plurality of images in adjacent frames according to the value of the target work of breathing, a degree of the differentiation based on a number of the adjacent frames being positively correlated to the value of the target work of breathing.

7. The method of claim 2, further comprising:
outputting, according to a pre-set rule, monitoring data and a trend of changes in the monitoring data within a pre-set time period before a current time, the monitoring data comprising at least one of the ventilation volume, the lung compliance, the thoracic compliance, or the target work of breathing.

8. The method of claim 7, wherein the monitoring data comprises a time within a last respiratory cycle before a current respiratory cycle.

9. The method of claim 1, wherein sizes of the plurality of images remain unchanged.

10. A device for state display during a ventilation process, comprising:
a first processor configured for determining a monitoring parameter regarding a user;
a second processor configured for determining a respiration state of the user, the respiration state comprising an exhalation state and an inhalation state;
a first display coupled to the first processor and configured to display a plurality of images, corresponding to the monitoring parameter, according to a pre-set correlation, to facilitate timely adjustment of a therapy strategy applied to the user; and
a second display coupled to the first and second processors and configured to:
in response to the monitoring parameter comprising a first monitoring parameter, display a continuous change in a first transparency of the plurality of images according to the respiration state and the first monitoring parameter, the continuous change in the first transparency being configured to enable determination of whether the respiration state is an exhalation state or an inhalation state; and
in response to the monitoring parameter comprising a second monitoring parameter, display a continuous change in a second transparency of the plurality of images according to the respiration state and the second monitoring parameter, the continuous change in the second transparency being different from the continuous change in the first transparency.

11. The device of claim 10, wherein the monitoring parameter comprises at least one of ventilation volume, lung compliance, thoracic compliance, or target work of breathing; and
the target work of breathing comprises at least one of work of breathing of the user or work of breathing of a ventilator.

12. The device of claim 11, wherein the plurality of images comprise a first lung image, and the monitoring parameter comprises the ventilation volume; and
wherein the first display is configured to display the first lung image, corresponding to the ventilation volume, according to a correlation between a value of the ventilation volume and a position of a pre-set plot in the first lung image.

13. The device of claim 11, wherein the monitoring parameter comprises the lung compliance, and the plurality of images comprise a second lung image, and
wherein the first display is configured to perform at least one of:
displaying the second lung image corresponding to the lung compliance according to a correlation between a value of the lung compliance and a color of a lung contour in the second lung image;
displaying the second lung image corresponding to the lung compliance according to a correlation between a value of the lung compliance and a thickness of the lung contour in the second lung image; or
displaying the second lung image corresponding to the lung compliance according to a correlation between a value of the lung compliance and a third transparency of the second lung image,
wherein sizes of the plurality of images that comprise the second lung image remain unchanged.

14. The device of claim 11, wherein the monitoring parameter comprises the thoracic compliance, and the plurality of images comprise a first thoracic image, and
 wherein the first display is configured to perform at least one of:
  displaying the first thoracic image corresponding to the thoracic compliance according to a correlation between a value of the thoracic compliance and a color of a thoracic contour in the first thoracic image;
  displaying the first thoracic image corresponding to the thoracic compliance according to a correlation between a value of the thoracic compliance and a thickness of the thoracic contour in the first thoracic image; or
  displaying the first thoracic image corresponding to the thoracic compliance according to a correlation between a value of the thoracic compliance and a fourth transparency in the first thoracic image.

15. The device of claim 11, wherein the monitoring parameter comprises the target work of breathing, and
 wherein the first display is configured to perform at least one of:
  displaying the plurality of images according to output smoothness which is inversely correlated to a value of the target work of breathing; or
  differentially displaying the plurality of images in adjacent frames according to the value of the target work of breathing, a degree of the differentiation based on a number of the adjacent frames being positively correlated to the value of the target work of breathing.

16. The device of claim 11, further comprising:
 an output interface configured to output, according to a pre-set rule, monitoring data and a trend of changes in the monitoring data within a pre-set time period before a current time, the monitoring data comprising at least one of the ventilation volume, the lung compliance, the thoracic compliance, or the target work of breathing.

17. The device of claim 16, wherein the monitoring data comprises a time within a last respiratory cycle before a current respiratory cycle.

18. The device of claim 10,
 wherein sizes of the plurality of images remain unchanged.

19. A ventilator, comprising a device for state display during a ventilation process, the device comprising:
 a processor configured for determining a monitoring parameter regarding a user; and
 a display configured for displaying a lung image corresponding to the monitoring parameter, according to a pre-set correlation, to facilitate timely adjustment of a therapy strategy applied to the user,
 wherein:
 the lung image comprises a lung contour, and the monitoring parameter comprises ventilation volume;
 the processor is configured to set a pre-set ventilation threshold according to conditions of the user and determine whether current ventilation volume of the user is excessive or inadequate based on comparison with the pre-set ventilation threshold, the pre-set ventilation threshold being determined by a ventilation requirement of the user;
 in response to determining that the current ventilation volume of the user is excessive, the display displays a line at an inner edge of the lung contour; and
 in response to determining that the current ventilation volume of the user is inadequate, the display displays the line at an outer edge of the lung contour, thereby assisting a ventilation adjustment and avoiding undesirable ventilation therapy.

20. The ventilator of claim 19, wherein the monitoring parameter further comprises at least one of lung compliance, thoracic compliance, or target work of breathing; and
 the target work of breathing comprises at least one of work of breathing of the user or work of breathing of a ventilator.

* * * * *